US012784878B2

(12) United States Patent
Clyde et al.

(10) Patent No.: US 12,784,878 B2
(45) Date of Patent: Nov. 3, 2026

(54) SYSTEMS AND METHODS FOR REINFORCEMENT LEARNING MOLECULAR MODELING

(71) Applicant: UCHICAGO ARGONNE, LLC, Chicago, IL (US)

(72) Inventors: Austin Robert Clyde, Chicago, IL (US); Arvind Ramanathan, Naperville, IL (US); Rick Stevens, Plainfield, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 508 days.

(21) Appl. No.: 17/244,711

(22) Filed: Apr. 29, 2021

(65) Prior Publication Data

US 2022/0351808 A1 Nov. 3, 2022

(51) Int. Cl.

| | |
|---|---|
| ***G16C 20/30*** | (2019.01) |
| ***G16B 5/20*** | (2019.01) |
| ***G16B 15/30*** | (2019.01) |
| ***G16B 40/00*** | (2019.01) |
| ***G16C 20/70*** | (2019.01) |

(52) U.S. Cl.

CPC ............... *G16C 20/30* (2019.02); *G16B 5/20* (2019.02); *G16B 15/30* (2019.02); *G16B 40/00* (2019.02); *G16C 20/70* (2019.02)

(58) Field of Classification Search

None

See application file for complete search history.

(56) References Cited

U.S. PATENT DOCUMENTS

| | | | |
|---|---|---|---|
| 6,792,356 B2 | 9/2004 | Mayo et al. | |
| 8,036,867 B2 | 10/2011 | Prakash et al. | |
| 10,665,324 B2 | 5/2020 | Fleishman et al. | |
| 10,776,712 B2 | 9/2020 | Oono et al. | |
| 2016/0057621 A1 | 2/2016 | Bovet | |
| 2019/0272468 A1 | 9/2019 | Feinberg et al. | |
| 2019/0272887 A1 | 9/2019 | Feinberg et al. | |
| 2020/0020415 A1* | 1/2020 | Sarmiento | G16B 40/00 |

(Continued)

FOREIGN PATENT DOCUMENTS

| | | |
|---|---|---|
| WO | WO-2017/070160 A1 | 4/2017 |
| WO | WO-2019/100158 A1 | 5/2019 |

(Continued)

OTHER PUBLICATIONS

De Vivo, M., Masetti, M., Bottegoni, G., & Cavalli, A. (2016). Role of molecular dynamics and related methods in drug discovery. Journal of medicinal chemistry, 59(9), 4035-4061. (Year: 2016).*

(Continued)

*Primary Examiner* — Karlheinz R. Skowronek
*Assistant Examiner* — Mary C Leverett
(74) *Attorney, Agent, or Firm* — Foley & Lardner LLP

(57) ABSTRACT

A system can include one or more processors configured to identify a candidate molecule, provide the candidate molecule as an input to a simulation, operate the simulation, monitor at least one parameter of the simulation, modify the candidate molecule based on the at least one parameter, and output the modified candidate molecule responsive to a convergence condition being satisfied.

20 Claims, 4 Drawing Sheets

(56) References Cited

U.S. PATENT DOCUMENTS

2021/0057050 A1* 2/2021 Zavoronkovs ....... C07D 471/10

FOREIGN PATENT DOCUMENTS

WO WO-2020/086604 A1 4/2020
WO WO-2020/140156 A1 7/2020

OTHER PUBLICATIONS

Elton, Daniel C., et al. "Deep learning for molecular design—a review of the state of the art." Molecular Systems Design & Engineering 4.4 (2019): 828-849. (Year: 2019).*
Pereira, Tiago, et al. "Diversity oriented deep reinforcement learning for targeted molecule generation." Journal of cheminformatics 13.1 (2021): 21. (Year: 2021).*
Zhou, Zhenpeng, et al. "Optimization of molecules via deep reinforcement learning." Scientific reports 9.1 (2019): 10752. (Year: 2019).*
Liu, Xuewei, et al. "Molecular dynamics simulations and novel drug discovery." Expert opinion on drug discovery 13.1 (2018): 23-37. (Year: 2018).*
Braun, E., et al. "Best Practices for Foundations in Molecular Simulations [Article v1.0] " Living J Comput Mol Sci. 2019; 1(1):. doi:10.33011/livecoms.1.1.5957. (Year: 2019).*
Hollingsworth, Scott A., and Ron O. Dror. "Molecular dynamics simulation for all." Neuron. Sep. 19, 2018; 99(6): 1129-1143. doi:10.1016/j.neuron.2018.08.011 (Year: 2019).*
Jeon, Woosung, and Dongsup Kim. "Autonomous molecule generation using reinforcement learning and docking to develop potential novel inhibitors." Scientific reports 10.1 (2020): 22104. (Year: 2020).*
Gioia, Dario, et al. "Dynamic docking: a paradigm shift in computational drug discovery." Molecules 22.11 (2017): 2029. (Year: 2017).*
Amaro, et al., "An improved relaxed complex scheme for receptor flexibility in computer-aided drug design," Journal of Computer-Aided Molecular Design 22, pp. 693-705 (2008).
Baron & Mccammon, "(Thermo)dynamic Role of Receptor Flexibility, Entropy, and Motional Correlation in Protein-Ligand Binding," ChemPhysChem 9(7), pp. 983-988 (2008).
Bohacek, et al., "The art and practice of structure-based drug design: A molecular modeling perspective," Medicinal Research Reviews 16(1), pp. 3-50 (1996).
Brameld, et al., "Small Molecule Conformational Preferences Derived from Crystal Structure Data. A Medicinal Chemistry Focused Analysis," Journal of Chemical Information and Modeling 48(1), pp. 1-24 (2008).
Chodera, "A Simple Method for Automated Equilibration Detection in Molecular Simulations," Journal of Chemical Theory and Computation 12(4), pp. 1799-1805 (2016).
Codera & Shirts, "Replica exchange and expanded ensemble simulations as Gibbs sampling: Simple improvements for enhanced mixing," The Journal of Chemical Physics 135(19), 194110, 15 pages (2011).
Comitani & Gervasio, "Modeling ligand-target binding with enhanced sampling simulations," Biomolecular Simulations in Structure-Based Drug Discovery, pp. 45-66 (2018).
Eastman & Pande, "Constant Constraint Matrix Approximation: A Robust, Parallelizable Constraint Method for Molecular Simulations," Journal of Chemical Theory and Computation 6(2), pp. 434-437 (201).
Eastman & Pande, "Efficient nonbonded interactions for molecular dynamics on a graphics processing unit," Journal of Computational Chemistry 31(6), pp. 1268-1272 (2010).
Eastman, et al., "OpenMM 7: Rapid development of high performance algorithms for molecular dynamics," PLoS Computational Biology 13(7):e1005659, 17 pages (2017).
Eastman, et al., "OpenMM: A Hardware-Independent Framework for Molecular Simulations," Computing in Science & Engineering 12(4), pp. 34-39 (2010).
Elton, et al., "Deep learning for molecular design—a review of the state of the art," retrieved from https://arxiv.org/abs/1903.04388, 24 pages (2019).
Erlanson, et al., "Fragment-Based Drug Discovery," Journal of Medicinal Chemistry 47(14), pp. 3463-3482 (2004).
Ertl & Schuffenhauer, "Estimation of synthetic accessibility score of drug-like molecules based on molecular complexity and fragment contributions," Journal of Cheminformatics 1:8, 11 pages (2009).
Friedrichs, et al., "Accelerating molecular dynamic simulation on graphics processing units," Journal of Computational Chemistry 30(6), pp. 864-872 (2009).
Haarnoja, et al., "Soft Actor-Critic: Off-Policy Maximum Entropy Deep Reinforcement Learning with a Stochastic Actor," Proceedings of Machine Learning Research 80, pp. 1861-1870 (2018).
Hughes, et al., "Principles of early drug discovery," British Journal of Pharmacology 162(6), pp. 1239-1249 (2011).
Jia, et al., "Anthropogenic biases in chemical reaction data hinder exploratory inorganic synthesis," Nature 573, pp. 251-255 (2019).
Jorgensen, et al., "Comparison of simple potential functions for simulating liquid water," The Journal of Chemical Physics 79(2), pp. 926-935 (1983).
Lin, et al., "Computational Drug Design Accommodating Receptor Flexibility: The Relaxed Complex Scheme," Journal of the American Chemical Society 124(20), pp. 5632-5633 (2002).
Lin, et al., "The relaxed complex method: Accommodating receptor flexibility for drug design with an improved scoring scheme," Biopolymers 68(1), pp. 47-62 (2003).
Lyne, "Structure-based virtual screening: an overview," Drug Discovery Today 7(20), pp. 1047-1055 (2002).
Lyu, et al., "Ultra-large library docking for discovering new chemotypes," Nature 566, pp. 224-229 (2019).
Maier, et al., "ff14SB: Improving the Accuracy of Protein Side Chain and Backbone Parameters from ff99SB," Journal of Chemical Theory and Computation 11(8), pp. 3696-3713 (2015).
Mattedi, et al., "Understanding Ligand Binding Selectivity in a Prototypical GPCR Family," Journal of Chemical Information and Modeling 59(6), pp. 2830-2836 (2019).
Mcgann, "FRED Pose Prediction and Virtual Screening Accuracy," Journal of Chemical Information and Modeling 51(3), pp. 578-596 (2011).
Mcgann, et al., "Gaussian docking functions," Biopolymers 68(1), pp. 76-90 (2003).
Miller, et al., "MMPBSA.py: An Efficient Program for End-State Free Energy Calculations," Journal of Chemical Theory and Computation 8(9), pp. 314-3321 (2012).
Minnich, et al., "AMPL: A Data-Driven Modeling Pipeline for Drug Discovery," Journal of Chemical Information and Modeling 60(4), pp. 1955-1968 (2020).
Mirza, et al., "Virtual screening of eighteen million compounds against dengue virus: Combined molecular docking and molecular dynamics simulations study," Journal of Molecular Graphics and Modelling 66, pp. 99-107 (2016).
Murray & Rees, "Opportunity Knocks: Organic Chemistry for Fragment-Based Drug Discovery (FBDD)," Angewante Chemie 55(2), pp. 488-492 (2016).
Murray & Rees, "The rise of fragment-based drug discovery," Nature Chemistry 1, pp. 187-192 (2009).
Mysinger, et al., "Directory of Useful Decoys, Enhanced (DUD-E): Better Ligands and Decoys for Better Benchmarking," Journal of Medicinal Chemistry 55(14), pp. 6582-6594 (2012).
Nichols, et al., "Predictive Power of Molecular Dynamics Receptor Structures in Virtual Screening," Journal of Chemical Information and Modeling 51(6), pp. 1439-1446 (2011).
Nichols, et al., "Rational Prediction with Molecular Dynamics for Hit Identification," Current Topics in Medicinal Chemistry 12(18), pp. 2002-2012 (2012).
Nilmeier, et al., "Nonequilibrium candidate Monte Carlo is an efficient tool for equilibrium simulation," Proceedings of the National Academy of Sciences 108(45), pp. E1009-E1018 (2011).

(56) References Cited

OTHER PUBLICATIONS

Noe, et al., “Machine Learning for Molecular Simulation,” Annual Review of Physical Chemistry 71, pp. 361-390 (2020).
Okimoto, et al., “High-Performance Drug Discovery: Computational Screening by Combining Docking and Molecular Dynamics Simulations,” PLoS Computational Biology 5(10), e1000528, 13 pages (2009).
Oprea & Matter, “Integrating virtual screening in lead discovery,” Current Opinion in Chemical Biology 8(4), pp. 349-358 (2004).
Oprea, “Virtual Screening in Lead Discovery: A Viewpoint,” Molecules 7(1), pp. 51-62 (2002).
Popova, et al., “Deep reinforcement learning for de novo drug design,” Science Advances 4(7), eaap7885, 14 pages (2018).
Rick, “Increasing the Efficiency of Free Energy Calculations Using Parallel Tempering and Histogram Reweighting,” Journal of Chemical Theory and Computation 2(4), pp. 939-946 (2006).
Roe & Cheatham, “PTRAJ and CPPTRAJ: Software for Processing and Analysis of Molecular Dynamics Trajectory Data,” Journal of Chemical Theory and Computation 9(7), pp. 3084-3095 (2013).
Schulman, et al., “Proximal Policy Optimization Algorithms,” retrieved from https://arxiv.org/abs/1707.06347, 12 pages (2017).
Schulman, et al., “Trust Region Policy Optimization,” Proceedings of Machine Learning Research 37, pp. 1889-1897 (2015).
Shukla, et al., “Structure-based screening and molecular dynamics simulations offer novel natural compounds as potential inhibitors of *Mycobacterium tuberculosis* isocitrate lyase,” Journal of Biomolecular Structure and Dynamics 36(8), pp. 2045-2057 (2017).
Sivanesan, et al., “In-silico Screening using Flexible Ligand Binding Pockets: A Molecular Dynamics-based Approach,” Journal of Computer-Aided Molecular Design 19, 213-228 (2005).
Stoter, et al., “CellProfiler and KNIME: Open Source Tools for High Content Screening,” Target Identification and Validation in Drug Discovery, pp. 105-122 (2013).
Suruzhon, et al., “ProtoCaller: Robust Automation of Binding Free Energy Calculations,” Journal of Chemical Information and Modeling 60(4), pp. 1917-1921 (2020).
Tsubaki, et al., “Compound-protein interaction prediction with end-to-end learning of neural networks for graphs and sequences,” Bioinformatics 35(2), pp. 309-318 (2019).
Van Hasselt, et al., “Deep Reinforcement Learning with Double Q-Learning,” Proceedings of the AAAI Conference on Artificial Intelligence 30(1), pp. 2094-2100 (2016).
Verkhivker, et al., “Parallel simulated tempering dynamics of ligand-protein binding with ensembles of protein conformations,” Chemical Physics Letters 337(1-3), pp. 181-189 (2001).
Wang, et al., “Development and testing of a general amber force field,” Journal of Computational Chemistry 25(9), pp. 1157-1174 (2004).
Wang, et al., “Identifying ligand binding sites and poses using GPU-accelerated Hamiltonian replica exchange molecular dynamics,” Journal of Computer-Aided Molecular Design 27, pp. 989-1007 (2013).
Warren, et al., “A Critical Assessment of Docking Programs and Scoring Functions,” Journal of Medicinal Chemistry 49(20), pp. 5912-5931 (2006).
Woods, et al., “Replica-Exchange-Based Free-Energy Methods,” New Algorithms for Macromolecular Simulation, pp. 251-259 (2006).
Yang, et al., “Target discovery from data mining approaches,” Drug Discovery Today 17, pp. S16-S23 (2012).

* cited by examiner

200

200a

200b

200c

200d

SYSTEMS AND METHODS FOR REINFORCEMENT LEARNING MOLECULAR MODELING

STATEMENT OF GOVERNMENT INTEREST

This invention was made with government support under Contract No. DE-AC02-06CH11357 awarded by the United States Department of Energy to UChicago Argonne, LLC, operator of Argonne National Laboratory. The government has certain rights in the invention.

TECHNICAL FIELD

The present invention relates generally to the field of molecular dynamics simulation, and more particularly to systems and methods for reinforcement learning molecular modeling.

BACKGROUND

Computational methods can be used to evaluate and screen molecules as candidates for performing various functions, such as binding to particular sites on target proteins. The search space of candidate molecules may make it difficult to effectively select candidate molecules for particular functions through computational processes.

SUMMARY

At least one aspect relates to a method. The method can include identifying, by one or more processors, a candidate molecule; providing, by the one or more processors, the candidate molecule as an input to a simulation; operating, by the one or more processors, the simulation; monitoring, by the one or more processors, at least one parameter of the simulation; modifying, by the one or more processors, the candidate molecule based on the at least one parameter; and outputting, by the one or more processors, the modified candidate molecule responsive to a convergence condition being satisfied.

At least one aspect relates to a system. The system can include one or more processors configured to identify a candidate molecule, provide the candidate molecule as an input to a simulation, operate the simulation, monitor at least one parameter of the simulation, modify the candidate molecule based on the at least one parameter, and output the modified candidate molecule responsive to a convergence condition being satisfied.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

DETAILED DESCRIPTION

Figure 1:
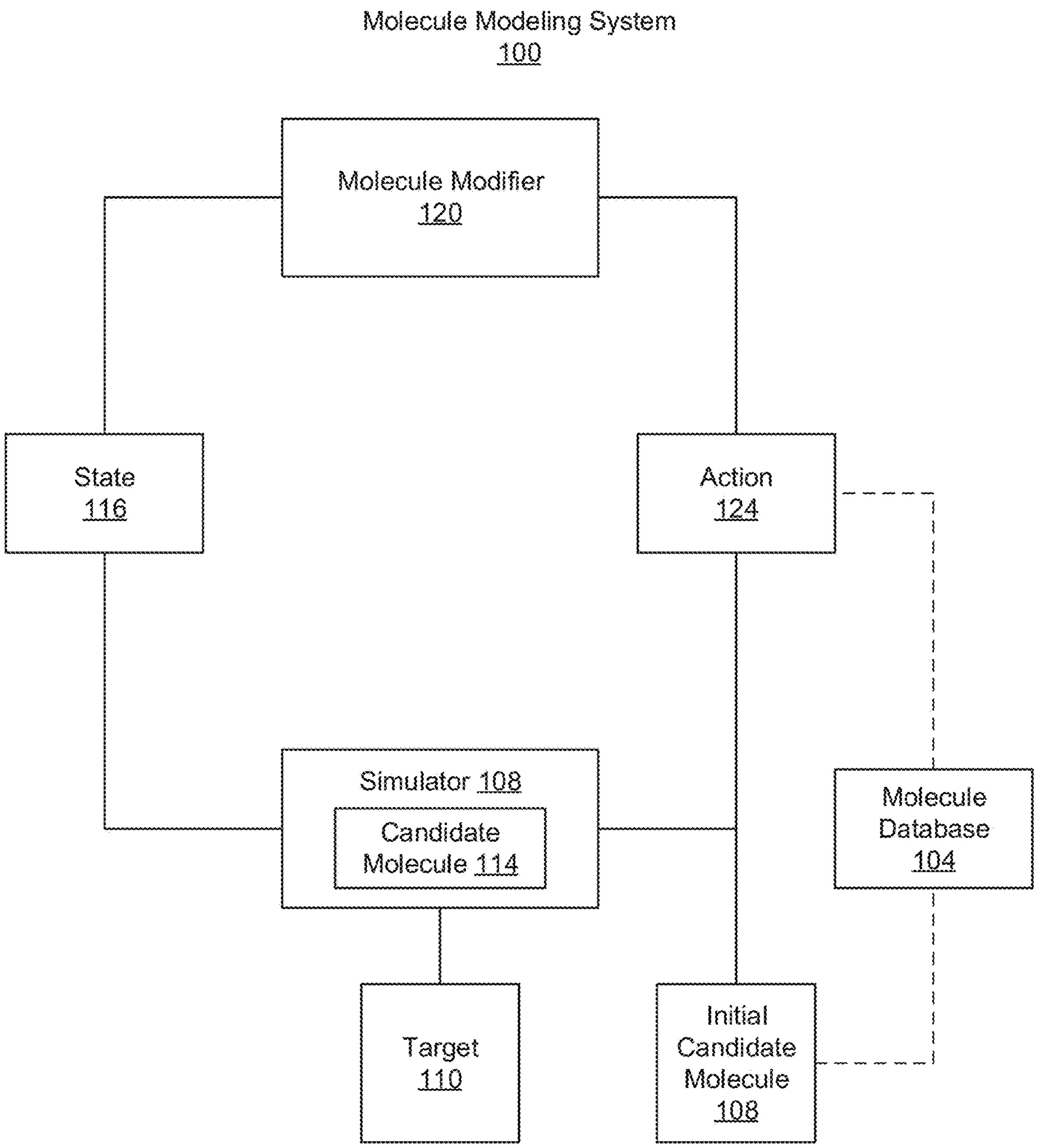
FIG. 1 is a block diagram of a molecular modeling system.

Embodiments described herein relate generally to systems and methods for reinforcement learning molecular modeling (RLMM). RLMM can be used to merge early stage drug discovery with late stage physics based molecular dynamics simulations to more effective evaluate and select candidate molecules.

Evaluation of synthetically feasible small molecule libraries has indicated that such libraries, when used for high throughput screening, can be biased to certain properties. Although it may be useful to expand the scope of molecules considered as candidates for functions such as binding to particular targets using computational approaches, the scope of molecules (e.g., $10^{60}$) will remain greater than computational resources can enumerate and screen. Some approaches use docking as a metric in order to identify candidates; however, docking can be a relatively imprecise or inaccurate metric for the actual affinity for the candidate, and may result in false positives or lack in compound availability. For example, some scoring functions including those based on docking may identify candidates that suggest high affinity, but may fail to sufficiently model the molecular interactions and processes, such as conformation factors that can determine the strength and stability of bonding, and thus can be limited in properly identifying and selecting candidate molecules for desired functions.

Embodiments described herein can perform artificial intelligence (AI) and machine learning (ML) processes to control molecular dynamics simulations, enabling more efficient screening of candidate molecules (e.g., ligands) along with realistic evaluation for performing desired functions or binding with targets. For example, a functional group can be changed based on detecting that the functional group is repelled from a pocket of the target; an external force can be provide to guide a ligand into particular position (which might otherwise require relatively long simulation time to occur); ligands can be driven into cryptic pockets or poses, such as those which would require large protein structural changes.

The molecular dynamics simulations can evaluate factors that address the true affinity of a candidate molecule for a target (e.g., including addressing that the target may not necessarily be a static object with a fixed binding site), such as protein flexibility and forces acting on the target from the ligand, as well as from other molecules and solvents in the environment, that determine whether conformation of a molecule is more or less likely at various time-steps. All atoms in the environment can be modeled by an equation and parameters, representing a force field. A state of the target can be evaluated as part of determining the ability of the ligand to bind to the target.

The molecular dynamics simulations can model state changes of the target, and the interacting forces between the ligand and the target, as well as other forces present in the environment. As such, system and methods described herein can sample various states of one or more binding sites of the target to identify candidate molecules likely to conform based on forces present in the simulation, and can reduce computational requirements associated with generation and selection of candidate molecules, enabling candidate molecules having desired properties to be efficiently generated in a manner that could not previously be achieved computationally.

For example, by implementing the machine learning models described herein, the use of molecular dynamics simulations to evaluate candidate molecules with greater fidelity and accuracy (e.g., realism with respect to actual binding and interaction of candidate molecules with targets) than other scoring methods can be enabled in a computationally efficient manner. For example, a method can be performed that includes identifying, by one or more processors, a candidate molecule, providing, by the one or more processors, the candidate molecule as an input to a simulation, operating, by the one or more processors, the simulation, monitoring, by the one or more processors, at least one parameter of the simulation, modifying, by the one or more processors, the candidate molecule based on the at least one parameter, and outputting, by the one or more processors, the modified candidate molecule responsive to a convergence condition being satisfied.

FIG. 1 depicts an example of a molecular modeling system (MMS) 100. The MMS 100 can be used to generate, screen, and select candidate molecules (e.g., ligands) for binding with targets (e.g., target molecules, such as target proteins). For example, the MMS 100 can perform molecular dynamics simulations between candidate molecules and targets, and modify or otherwise control the simulations using a policy controller, such as a machine learning model, that is trained to control features of at least one of the candidate molecule, the target, or the environment to more effectively detect and perform binding between the candidate molecule and the target.

The MMS 100 can be implemented using a processing circuit that includes one or more processors and memory. The processing circuit can include various components including graphics processing units (GPUs) and parallel computing components. The processor may be a general purpose or specific purpose processor, an application specific integrated circuit (ASIC), one or more field programmable gate arrays (FPGAs), a group of processing components, or other suitable processing components. The processor may be configured to execute computer code or instructions stored in memory (e.g., fuzzy logic, etc.) or received from other computer readable media (e.g., CDROM, network storage, a remote server, etc.) to perform one or more of the processes described herein. The memory may include one or more data storage devices (e.g., memory units, memory devices, computer-readable storage media, etc.) configured to store data, computer code, executable instructions, or other forms of computer-readable information. The memory may include random access memory (RAM), read-only memory (ROM), hard drive storage, temporary storage, non-volatile memory, flash memory, optical memory, or any other suitable memory for storing software objects and/or computer instructions. The memory may include database components, object code components, script components, or any other type of information structure for supporting the various activities and information structures described in the present disclosure. The memory may be communicably connected to the processor and may include computer code for executing one or more of the processes described herein. The memory can include various modules (e.g., circuits, engines) for completing processes described herein. The processing circuit can include wired or wireless communications electronics to communicate with other devices, such as remote databases.

The MMS 100 can include or be coupled with at least one molecule database 104. The molecule database 104 can maintain data structures representative of molecules, including but not limited to peptides, polypeptides, proteins, enzymes, and antibodies. The molecules can include small molecules, such as molecules having a molecular weight less than a threshold molecular weight or size (e.g., less than 900 daltons; a size on the order of 1 nanometer (nm) or less). The molecules can be represented as a crystal structure.

The molecule database 104 can include (or generate data structures based on information from) databases or software packages or programs such as the Protein Data Bank (e.g., RCSB Protein Data Bank), OpenMM Modeller and pdbfixer, and Open Eye Scientific SPRUCE. The MMS 100 can use information from various sources to add information missing from data structures of molecules, such as by using SPRUCE to fix initial structures from the Protein Data Bank that may include missing atoms, residues, clashes (e.g., inconsistent information), or other data that can affect downstream analysis of the molecules, such as parameterization using a force field.

The molecule database 104 can include a peptide fingerprint search database, enabling the molecule modifier 120 to generate actions 124 based on peptides retrieved from the fingerprint search database.

The MMS 100 can retrieve an initial candidate molecule 108 (e.g., a data structure representing the initial candidate molecule 108). The initial candidate molecule 108 can be retrieved from the molecule database 104. The initial candidate molecule 108 can be received as a user input, including based on user input indicating modification of a molecule retrieved from the molecule database 104.

The initial candidate molecule 108 can be a ligand, such as for simulating interaction between the initial candidate molecule 108 and a target 110. The initial candidate molecule 108 can be any of a variety of biomolecules, such as peptides, polypeptides, small molecules, or antibodies.

The initial candidate molecule 108 can have a docking score, binding affinity score, or other indication of an expectation of binding between the initial candidate molecule 108 and one or more binding sites of the target 110 that is less than a threshold score (e.g., a threshold score indicating that the initial candidate molecule 108 is not expect to bind with any of the one or more binding sites), such that the processes described herein can be used to modify the initial candidate molecule 108 into a modified candidate molecule that can effectively bind with the target 110 as determined using molecule dynamics simulations.

The target 110 can be a target molecule for achieving bonding between with the initial candidate molecule 108 (or candidate molecules 114 generated based on the MMS 100 modifying the initial candidate molecule 108 in one or more successive time-steps of the simulation as described herein). For example, the target 110 can be a protein having one or more binding sites, to which the initial candidate molecule 108 can be proposed for binding.

The MMS 100 can include a simulator 112. The simulator 112 can perform a molecular dynamics simulation. The molecular dynamics simulation can be performed to simulate interaction between at least one of a candidate molecule 114 (e.g., the initial candidate molecule 108; modified candidate molecules modified based on actions 124 generated by the molecule modifier 120 as described herein), the target 110, and an environment. The simulator 112 can include or be based on various molecular dynamics simulators, such as the Assisted Model Building with Energy Refinement (AMBER) simulator.

The environment can include molecules in addition to the candidate molecule 114 and the target 110 with which the candidate molecule 114 and the target 110 can interact. For example, the environment can include at least solvent in which the candidate molecule 114 and the target 110 are provided. The environment can define a three-dimensional coordinate space (e.g., Cartesian coordinate space) in which the candidate molecule 114 and the target 110 are provided.

The simulator 112 can define at least one parameter. The parameters can be parameters of the candidate molecule 114, the target 110, the environment, and interactions between one or more thereof. For example, the parameters can include temperature and pressure of the environment.

The parameters can include a potential, such as a force field value. The potential can be a value of potential energy for one or more interactions between components of the simulation, such as pair-wise or multi-body interactions between atoms or molecules of the simulation.

The simulator 112 can operate the simulation over a plurality of time-steps. For example, at a first time-step, the simulator 112 can define at least one state 116 of the simulation, which can include observations of the simulation, such as a first value of the at least one parameter and a position (e.g., Cartesian coordinate position) of each atom or molecule of the simulation. The state 116 can be a state of the simulation being performed by the simulator 112 at a particular time-step.

The simulator 112 can update, for a second time-step subsequent to the first time-step, the at least one parameter (e.g., to generate a second value) based on the first value and the positions of the molecules. For example, the simulator 112 can update the at least one parameter and the positions by evaluating the potential of the at least one parameter, which can indicate changes to kinetic energy of the atoms or molecules based on the potential, and thus changes to positions of the atoms or molecules. As such, the simulator 112 can define the state 116 for each time-step, and update the state 116 to generate the state 116 for a subsequent time-step (e.g., using various molecular dynamics simulation methods to be applied to the state 116, such as a Symplectic integrator or Verlet integrator).

The MMS 100 can include a molecule modifier 120. The molecule modifier 120 can receive the state 116 from the simulator 116 to monitor the simulator 116. The molecule modifier 120 can generate actions 124 to modify the candidate molecules (e.g., modify the initial candidate molecule 108 or candidate molecules previously modified during various time-steps of the simulation).

The molecule modifier 120 can be one or more models including one or more policies, heuristics, algorithms, rules, or other computational processes that generate the actions 124 based on the state 116, such as to satisfy a reward function. The molecule modifier 120 can use various combinations of models described herein, such as through weighting of various models (the weights can be weighted randomly to enable random generation of actions 124), to generate the actions 124.

For example, the molecule modifier 120 can be one or more machine learning models trained to select a perturbation of the candidate molecule 114 to satisfy the reward function, such as a reward function that minimizes total potential energy of the simulation.

The molecule modifier 120 can be trained during operation (e.g., without applying prior training data to the molecule modifier 120), For example, during operation of the MMS 100, at least one of a docking scorer or an expert policy (which can be used as the reward function) can be applied to the candidate molecule 114 to generate a docking score for the candidate molecule. As described further herein, the MMS 100 can operate (including using the docking scorer or expert policy to determine docking scores or other scores for candidate molecules 114) until a convergence condition is satisfied, during which one or more parameters, such as weights or biases, of the molecule modifier 120 can be modified to train the molecule modifier 120. The molecule modifier 120 can be trained using training data, such as training data that includes candidate molecules associated with reward function scores (e.g., predetermined reward function scores generated by a docking scorer, expert policy, or other scoring model or algorithm), such that the molecule modifier 120 can be trained by applying the candidate molecules as input to the molecule modifier 120, causing the molecule modifier 120 to generate actions 124 to be applied to the candidate molecules 114, comparing reward function scores of the candidate molecules 114 as modified by the actions 124 with the predetermined reward function scores, and modifying the molecule modifier 120 responsive to the comparison (e.g., modifying one or more weights or biases of the molecule modifier 120 using an optimization function or to satisfy a convergence condition). For example, from a particular state, the candidate molecule 114 may have twenty possible molecule changes (e.g., possible actions 124). The docking scorer, expert policy, or other scoring model or algorithm can be used during operation (or separately from operation) of the MMS 100 to determine a score (e.g., docking score) for each of the twenty possible changes, from which a best change can be selected based on the determined scores and used to train the molecule modifier 120 accordingly.

The reward function can be determined based on the state 116, such as by determining the total potential energy based on the potentials and positions of the atoms or molecules of the simulation represented by the state 116. The reward function can indicate an expectation of binding between the candidate molecule 114 and one or more binding sites of the target 110, such that meeting or exceeding a threshold value of the reward function can correspond to effective binding by the candidate molecule 114.

The molecule modifier 120 can include a reinforcement learning model, such as a model in which a state of the model is a current state of the candidate molecule and the action 124 to be generated is a change to be applied to the candidate molecule. For example the action 124 can include at least one of a swapping of a functional group or an addition of an external force to the system defined by the state 116.

For example, the molecule modifier 120 can include a deep Q-learning model, such as neural network operating on Equation 1:

$$Q_{t+1}(s_t, a_t) = Q_t(s_t, a_t) + a_t(s_t, a_t)r_t + \gamma \max_a Q_t\left(s_{t+1}, a_t\right) - Q_t(s_t, a_t) \quad \text{Equation 1}$$

The molecule modifier 120 can include at least one of a proximal policy optimization policy, a trust region policy optimization policy, or a soft actor-critic policy, each of which can be used (alone or in combination) to train the molecule modifier 120 to generate actions 124 expected to improve or optimize the reward function.

The molecule modifier 120 can generate the actions 124 to be at least partially random. For example, the molecule modifier 120 can randomly select amongst candidate actions 124 generated by various models and policies described herein.

For example, the molecule modifier 120 can generate the actions 124 to perform fragment growing of the candidate molecule 114. For example, the molecular modifier 120 can generate the actions 124 to identify one or more atoms or molecules to attach to the candidate molecule 114, such as to an end of the candidate molecule 114.

The molecule modifier 120 can generate the actions 124 using a three-dimensional (3D) color or shape database search. For example, the molecule modifier 120 can use the 3D color or shape database to identify similar molecules to the candidate molecule 114 based on color or shape data regarding the candidate molecule 114.

The molecule modifier 120 (or the simulator 108) can apply the actions 124 to the candidate molecule 114 to update the candidate molecule 114 for one or more subsequent time-steps of the simulation performed by the simulator 108.

The simulator 108 can perform the simulation, including advancing the simulation to subsequent time-steps and updating the candidate molecule 114 based on actions 124 generated by the molecule modifier 120, until a convergence condition is satisfied. The convergence condition can correspond to a value of the reward function, such as to operate the simulation until potential energy is maximized (or meets or exceeds a threshold value). The convergence condition can correspond to a total time of the simulation, such as a threshold number of time-steps. The simulator 108 can output the candidate molecule 114 responsive to the convergence condition being satisfied.

Figure 2A:
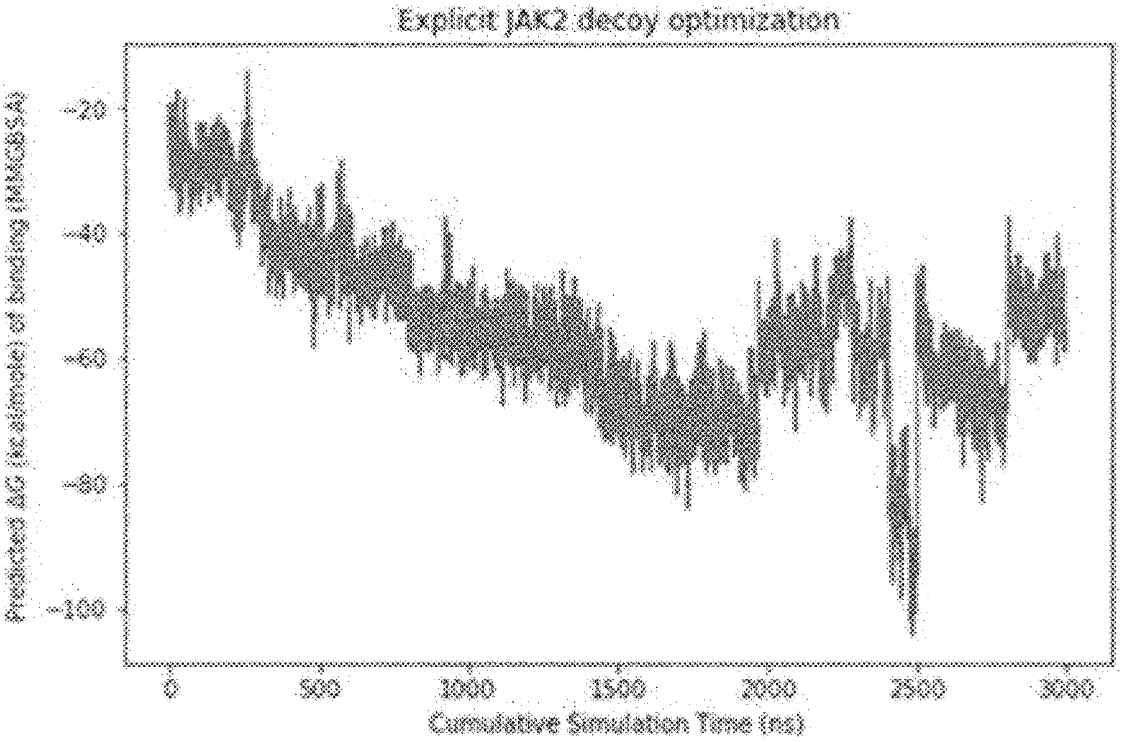
FIG. 2A-2B depict charts generated based on operation of a molecular modeling system.
Figure 2A:
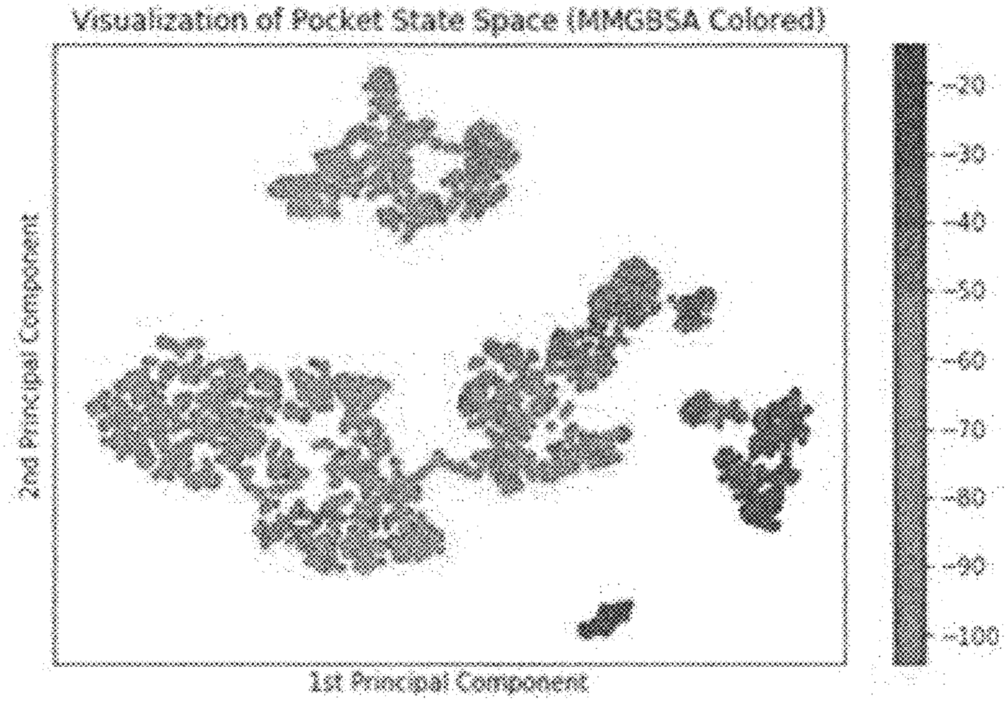
Figure 2B:
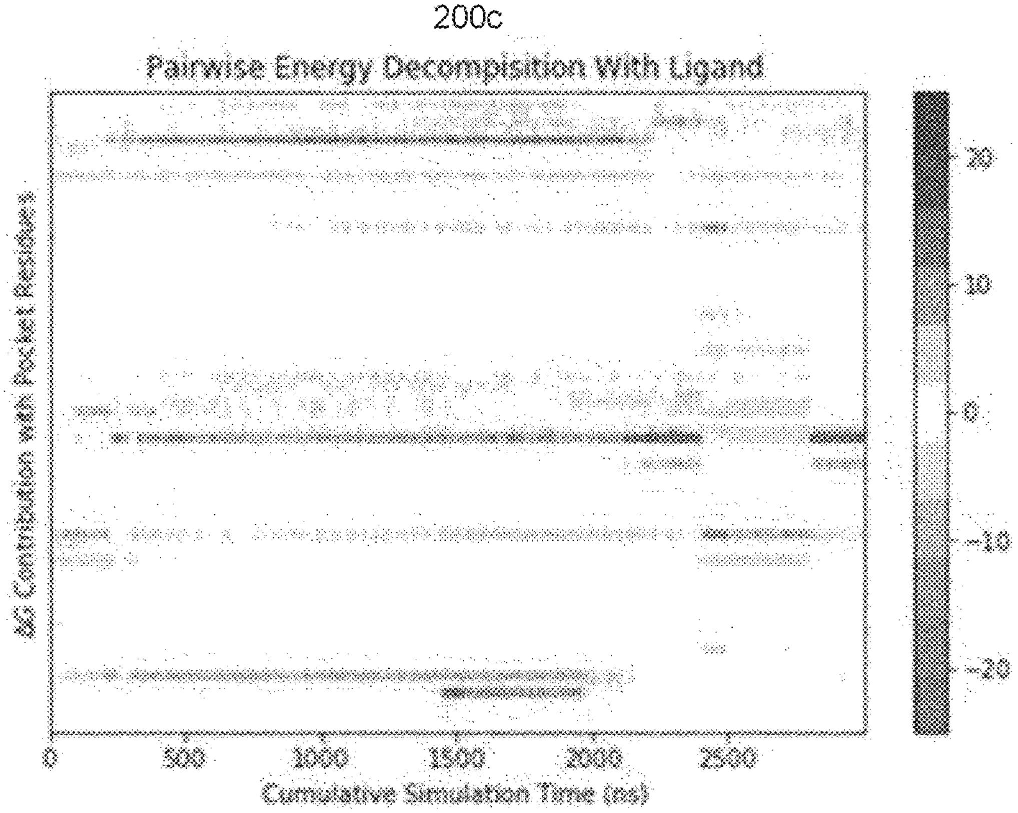
Figure 2B:
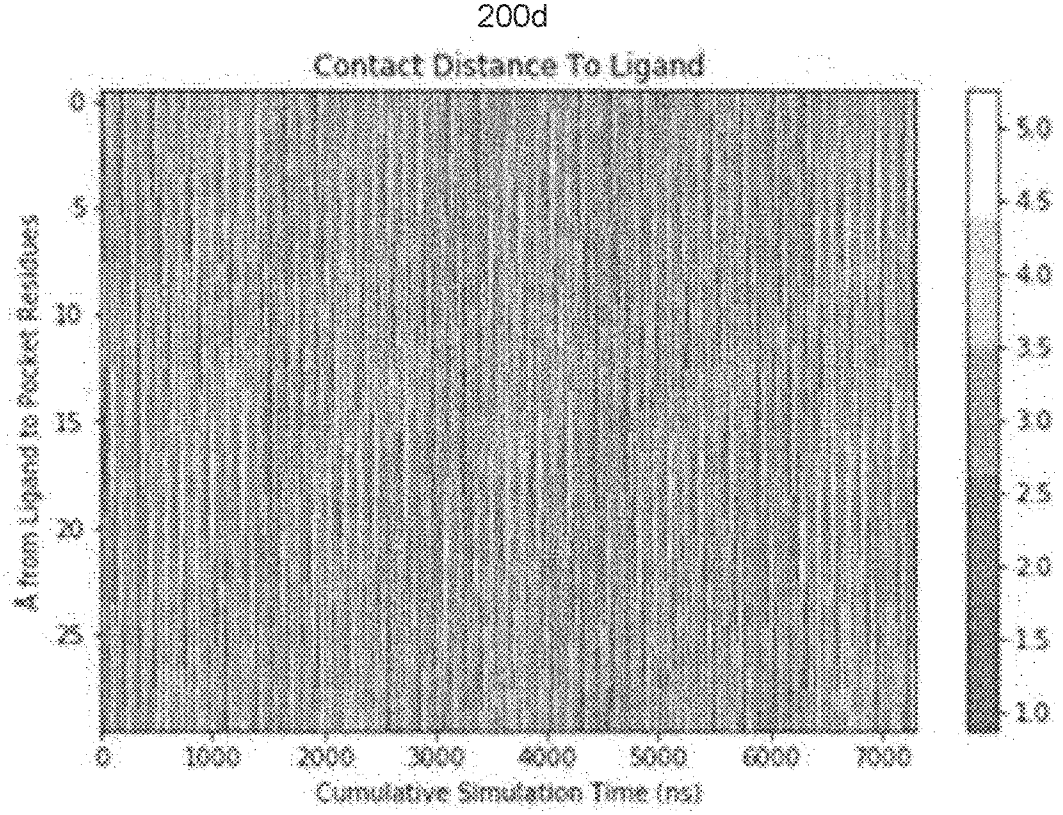

FIG. 2A-2B depict charts 200 based on using an example of the MMS 100 to generate a modified molecule based on an initial candidate molecule, validating the effectiveness of the MMS 100 for identifying candidate molecules that can effectively bind with target molecules (even if the initial candidate has less than a target level of binding despite other scoring methods, such as docking scores, suggesting that the initial candidate may be useful).

For example, the MMS 100 can be used to modify an initial candidate molecule that is a decoy compound for JAK2 kinase, and for which an initial docking score generated by CHEMGAUSS4 was not indicative of the fact that the initial candidate molecule was a decoy having a pose that met pose criteria based on visual inspection. Chart 200*a* depicts JAK2 decoy optimization over the course of the simulation, based on Gibbs free energy as the simulation advances. Chart 200*b* depicts pocket state spaces of the binding of the candidate molecule based on first and second principal components. Chart 200*c* depicts pairwise energy decomposition based on Gibbs free energy contributions with pocket residues of the target. Chart 200*d* depicts contact distance to the ligand (e.g., candidate molecule) over the course of the simulation.

Figure 3:
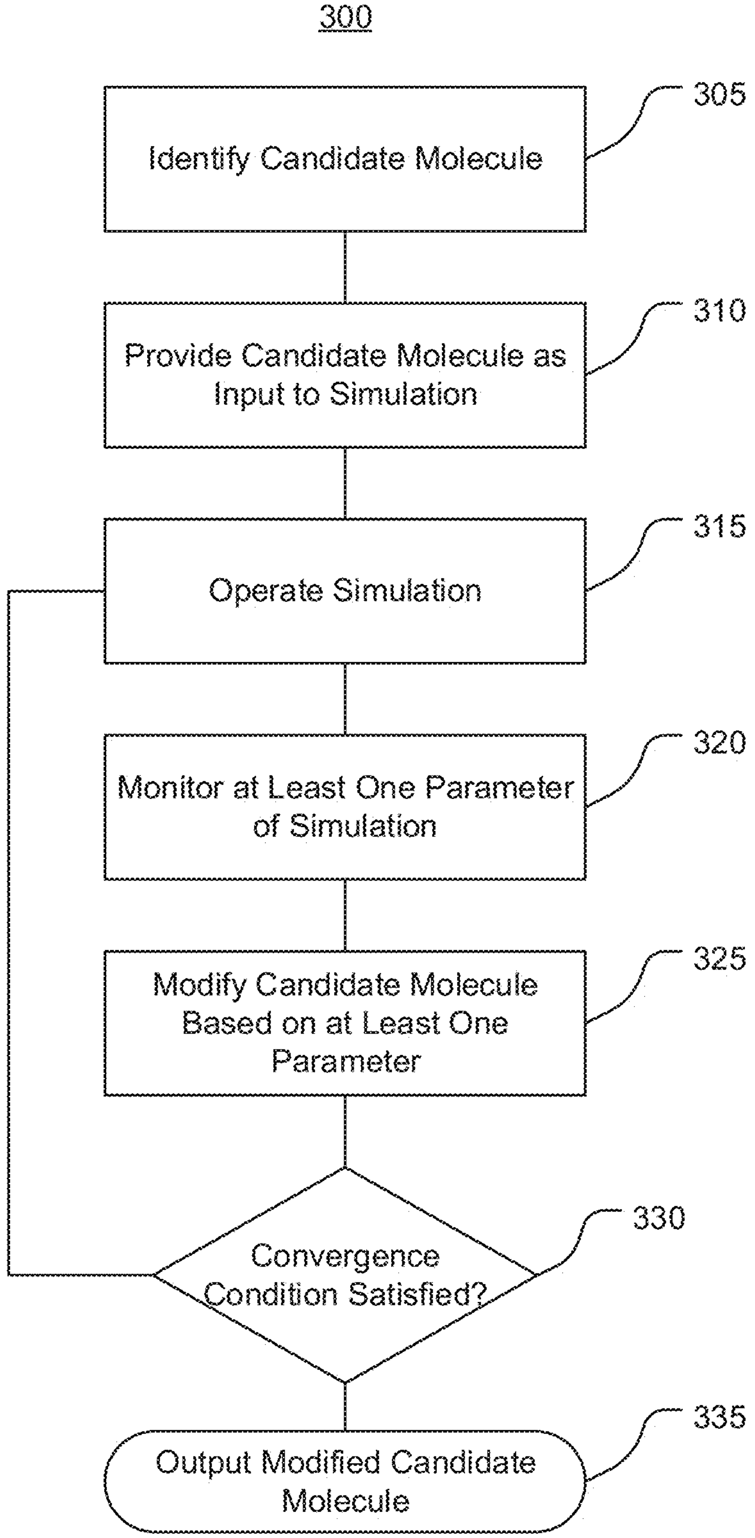
FIG. 3 is a flow of a method for molecular modeling.

FIG. 3 depicts an example of a method 300 for using reinforcement learning molecular modeling to modify and select candidate molecules, such as for binding with target proteins. The method 300 can be performed using various systems described herein, including the MMS 100. The method 300 can be performed using various computing systems, including parallel processing and cloud computing systems.

At 305, a candidate molecule is identified. The candidate molecule (e.g., initial candidate molecule) can be identified based on being received as user input, such as user input indicating an initial proposal of a candidate molecule for binding with a target, such as a target protein having one or more binding sites. The candidate molecule can be a small molecule, a peptide, a protein, or an antibody.

At 310, the candidate molecule is provided as input to a simulation. The simulation can be a simulation of interaction of the candidate molecule with an environment that includes a target, such as a protein to which the candidate molecule is to be attempted to bind. The target can include at least one binding site for binding with the candidate molecule. The simulation can simulate interactions such as binding energies (e.g., potentials) of the candidate molecule, the target, and any other molecules, such as solvents, present in an environment of the simulation. The simulation can be a molecular dynamics simulation.

At 315, the simulation is operated. Operating the simulation can include modelling interaction between the candidate molecule and the target, such as potentials (e.g., energy potentials) determined based on distances between the candidate molecule and the target. Operating the simulation can include updating parameters of the simulation, such as states, positions, velocities, orientations, energies, potentials, or other parameters regarding the candidate molecule and the target. For example, the simulation can be updated to advance from a first time-step to a second time-step subsequent to the first time step.

At 320, at least one parameter of the simulation can be monitored (e.g., observed). For example, parameters including state information from the simulation, such as distances and potentials associated with one or more molecules, or a total potential energy of the simulation, can be determined for each time-step of the simulation. Monitoring the at least one parameter can include observing (e.g., determining) values of rewards and parameters of the simulation.

At 325, the candidate molecule can be modified based on the at least one parameter. For example, various models, heuristics, policies, or algorithms can be applied, using the candidate molecule and the at least one parameter as an input, to generate an action that modifies a characteristic of the candidate molecule.

For example, a reinforcement learning model can be trained to generate an action to modify the candidate molecule expected to optimize a potential energy of at least one of the candidate molecule and the target, or expected to cause the candidate molecule to change state (e.g., move, change a functional group) to a state having a greater binding affinity with the target. Modifying the candidate molecule can include generating a plurality of modified candidate molecules, from which a subset of one or more selected candidate molecules can be selected (e.g., based on the value of the at least one parameter as applied to a reward function, such as a value of a binding affinity with the target).

At 330, responsive to modifying the candidate molecule, a convergence condition can be evaluated based on the modified candidate molecule, and the modified candidate molecule can be outputted responsive to a convergence condition being satisfied (335). The convergence condition can include a threshold value of a reward function, such as a reward function corresponding to an energy of the simulation. For example, the convergence condition can be satisfied responsive to the at least one parameter of the simulation indicating that a value of the reward function is greater than or equal to a threshold value. The convergence condition can be satisfied responsive to a threshold amount of time-steps of the simulation being performed.

Responsive to the convergence condition not being satisfied, the simulation can be operated (e.g., updated) using the modified candidate molecule. For example, the simulation can be updated for a subsequent time-step using the modified candidate molecule, such as to update positions, velocities, and other characteristics of the molecules of the simulation based on the modification to the candidate molecule. The candidate molecule can be iteratively modified over the course of advancing through multiple time-steps.

Definitions

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

The term "coupled," as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. Such members may be coupled mechanically, electrically, and/or fluidly.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit and/or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the fluid control systems and methods of fluid control as shown in the various exemplary embodiments is illustrative only. Additionally, any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. A method, comprising:

(a) identifying, by one or more processors, a candidate molecule for a target;

(b) providing, by the one or more processors, the candidate molecule and the target as inputs to a simulation;

(c) operating, by the one or more processors, the simulation, wherein operating the simulation comprises modelling interaction between the candidate molecule and the target over successive time steps of the simulation;

(d) monitoring, by the one or more processors, at least one state of the simulation at each successive time step;

(e) updating, by the one or more processors, for each time step of the successive time steps, a reinforcement learning model based on potential energy values of the at least one state of the simulation at each successive time step;

(f) generating, by the one or more processors, an action to the candidate molecule using the updated reinforcement learning model;

(g) modifying, by the one or more processors, the candidate molecule based on the action;

(h) updating, by the one or more processors, a parameter of the simulation based on the candidate molecule modified in step (g);

(i) repeating, by the one or more processors, with the candidate molecule modified in step (g) and the updated simulation in step (h), steps (b)-(h) until a convergence condition is satisfied; and (j) outputting, by the one or more processors, the modified candidate molecule responsive to the convergence condition being satisfied, the modified candidate molecule having a greater binding affinity for the target as compared to the candidate molecule.

2. The method of claim 1, wherein:

operating the simulation comprises operating a molecular dynamics simulation for a first time step and a second time step subsequent to the first time step;

monitoring the at least one state of the simulation at each successive time step comprises monitoring a first value of the at least one state of the simulation associated with the first time step; and modifying the candidate molecule comprises modifying a characteristic of the candidate molecule associated with the second time step based on the first value of the at least one state of the simulation associated with the first time step.

3. The method of claim 1, wherein the target is a target molecule.

4. The method of claim 1, wherein modifying the candidate molecule based on the at least one state of the simulation comprises modifying at least one of a functional group of the candidate molecule, an atom of the candidate molecule, or a pose of the candidate molecule.

5. The method of claim 1, wherein the at least one state of the simulation comprises at least one of a pose of the candidate molecule, a force between the candidate molecule and a target molecule, or an energy of the candidate molecule.

6. The method of claim 1, wherein generating the action to the candidate molecule using the updated reinforcement learning model comprises applying at least one of a policy or a model to the candidate molecule to generate a plurality of modified candidate molecules, and selecting the modified candidate molecule from the plurality of modified candidate molecules based on a score determined for the plurality of modified candidate molecules.

7. The method of claim 1, wherein the reinforcement learning model comprises a neural network.

8. The method of claim 1, wherein the candidate molecule comprises at least one of a protein, a peptide, a small molecule having a molecular weight less than a threshold molecular weight, or an antibody.

9. The method of claim 1, wherein the at least one state of the simulation comprises a binding affinity between the candidate molecule and a protein.

10. The method of claim 9, wherein the at least one state of the simulation comprises a distance between the candidate molecule and a binding site of the protein.

11. The method of claim 1, wherein the parameter of the simulation comprises a velocity of the modified candidate molecule.

12. A system, comprising:

one or more processors coupled with memory comprising processor-executable instructions to cause the one or more processors to:

(a) identify a candidate molecule for a target;

(b) provide the candidate molecule and the target as inputs to a simulation;

(c) operate the simulation, by modelling interaction between the candidate molecule and the target;

(d) monitor at least one state of the simulation;

(e) update a reinforcement learning model based on a potential energy value of the at least one state of the simulation;

(f) generate an action to the candidate molecule using the updated reinforcement learning model;

(g) modify the candidate molecule based on the action;

(h) update a parameter of the simulation based on the modified candidate molecule, the parameter comprising a position of the modified candidate molecule or a velocity of the modified candidate molecule;

(i) repeat, with the modified candidate molecule in step (g) and the updated simulation in step (h), steps (b)-(h) until a convergence condition is satisfied; and (j) output the modified candidate molecule responsive to the convergence condition being satisfied, the modified candidate molecule having a greater binding affinity for the target as compared to the candidate molecule.

13. The system of claim 12, wherein the processor-executable instructions are to cause the one or more processors to:

operate the simulation by operating a molecular dynamics simulation for a first time step and a second time step subsequent to the first time step;

monitor the at least one state of the simulation by monitoring a first value of the at least one state of the simulation associated with the first time step; and modify the candidate molecule by modifying a characteristic of the candidate molecule associated with the second time step based on the first value of the at least one state of the simulation associated with the first time step.

14. The system of claim 12, wherein the target comprises a target molecule.

15. The system of claim 12, wherein the processor-executable instructions are to cause the one or more processors to modify the candidate molecule based on the at least one state of the simulation by modifying at least one of a functional group of the candidate molecule, an atom of the candidate molecule, or a pose of the candidate molecule.

16. The system of claim 12, wherein the at least one state of the simulation comprises at least one of a pose of the candidate molecule, a force between the candidate molecule and a target molecule, or an energy of the candidate molecule.

17. The system of claim 12, wherein the processor-executable instructions are to cause the one or more processors to generate the action to the candidate molecule using the updated reinforcement learning model by applying the updated reinforcement learning model that applies at least one of a policy or a model to the candidate molecule to generate a plurality of modified candidate molecules, and select the modified candidate molecule from the plurality of modified candidate molecules based on a score determined for the plurality of modified candidate molecules.

18. The system of claim 12, wherein the reinforcement learning model comprises a deep Q-learning model.

19. The system of claim 12, wherein the candidate molecule comprises at least one of a protein, a peptide, a small molecule having a molecular weight less than a threshold molecular weight, or an antibody.

20. The system of claim 12, wherein the at least one state of the simulation comprises a binding affinity between the candidate molecule and a protein.

* * * * *